US012727852B2

(12) United States Patent
Funka-Lea et al.

(10) Patent No.: US 12,727,852 B2
(45) Date of Patent: Sep. 8, 2026

(54) LEFT ATRIAL APPENDAGE ASSESSMENT METHOD

(71) Applicant: Siemens Medical Solutions USA, Inc., Malvern, PA (US)

(72) Inventors: Gareth Funka-Lea, Princeton, NJ (US); Athira Jane Jacob, Plainsboro, NJ (US); Paul Klein, Princeton, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 18/889,729

(22) Filed: Sep. 19, 2024

(65) Prior Publication Data

US 2026/0076646 A1 Mar. 19, 2026

(51) Int. Cl.

*A61B 8/12* (2006.01)
*A61B 8/00* (2006.01)
(Continued)

(52) U.S. Cl.

CPC .............. *A61B 8/12* (2013.01); *A61B 8/0883* (2013.01); *A61B 8/463* (2013.01); *A61B 8/466* (2013.01); *A61B 8/5223* (2013.01); *A61B 8/5253* (2013.01); *G06T 7/10* (2017.01); *G06T 7/38* (2017.01); *G06T 7/62* (2017.01);
(Continued)

(58) Field of Classification Search

CPC ......... A61B 8/12; A61B 8/0883; A61B 8/463; A61B 8/466; A61B 8/5223; A61B 8/5253; A61B 2576/023; G06T 7/10; G06T 7/38; G06T 7/62; G06T 2200/08; G06T 2207/10132; G06T 2207/20084;
(Continued)

(56) References Cited

U.S. PATENT DOCUMENTS

| | | | |
|---|---|---|---|
| 7,831,076 | B2 | 11/2010 | Altmann et al. |
| 10,524,765 | B2 | 1/2020 | Hill et al. |

(Continued)

FOREIGN PATENT DOCUMENTS

| | | | |
|---|---|---|---|
| JP | 2008183398 | A | 8/2008 |
| JP | 2013544176 | A | 12/2013 |

(Continued)

OTHER PUBLICATIONS

Jens Erik Nielsen-Kudsk et al.; Intracardiac Echocardiography to Guide Watchman FLX Implantation: The ICE LAA Study; JACC Cardiovascular Interventions; 2023; vol. 16; pp. 643-651.

(Continued)

*Primary Examiner* — Michael J Carey
*Assistant Examiner* — Maria Christina Talty

(57) ABSTRACT

Systems and methods for left atrial appendage closure device specification from two dimensional (2D) Intracardiac Echo imaging (ICE). In an imaging procedure, 2D ICE is used to acquire images of the left atrium of a patient. A model of the left atrium is generated from the images of the left atrium. The model of the left atrium is used to validate subsequent imaging of the left atrial appendage of the patient. Anatomical measurements from the validated subsequent imaging may be used to select or specify a left atrial appendage closure device in order to, for example, treat atrial fibrillation patients.

12 Claims, 9 Drawing Sheets

(51) Int. Cl.

| | |
|---|---|
| ***A61B 8/08*** | (2006.01) |
| ***G06T 7/10*** | (2017.01) |
| ***G06T 7/38*** | (2017.01) |
| ***G06T 7/62*** | (2017.01) |
| ***G16H 20/40*** | (2018.01) |

(52) U.S. Cl.
CPC ........ *G16H 20/40* (2018.01); *A61B 2576/023* (2013.01); *G06T 2200/08* (2013.01); *G06T 2207/10132* (2013.01); *G06T 2207/20084* (2013.01); *G06T 2207/20212* (2013.01); *G06T 2207/30048* (2013.01)

(58) Field of Classification Search
CPC ........... G06T 2207/20212; G06T 2207/30048; G16H 20/40
See application file for complete search history.

(56) References Cited

U.S. PATENT DOCUMENTS

| | | | | |
|---|---|---|---|---|
| 11,450,003 | B2 | 9/2022 | Li et al. | |
| 11,534,136 | B2 | 12/2022 | Funka-lea | |
| 11,922,621 | B2 | 3/2024 | Urman et al. | |
| 12,283,052 | B2 | 4/2025 | Bhowmick et al. | |
| 12,478,436 | B2 | 11/2025 | Liao et al. | |
| 2015/0164605 | A1* | 6/2015 | Patwardhan | A61B 90/37 600/417 |
| 2019/0090951 | A1* | 3/2019 | Camus | A61B 8/483 |
| 2021/0322103 | A1* | 10/2021 | Mortier | G16H 50/30 |
| 2022/0330921 | A1* | 10/2022 | Miyaki | A61B 8/5207 |
| 2023/0119535 | A1 | 4/2023 | Michiels et al. | |
| 2023/0240656 | A1 | 8/2023 | Agarwal et al. | |

FOREIGN PATENT DOCUMENTS

| | | | | |
|---|---|---|---|---|
| JP | 2020068797 A | 5/2020 | | |
| JP | 2022168851 A | 11/2022 | | |
| JP | 2023511300 A | 3/2023 | | |
| JP | 2023077407 A | 6/2023 | | |
| JP | 2023531981 A | 7/2023 | | |
| WO | 2023100979 A1 | 6/2023 | | |
| WO | WO-2024013114 A1 * | 1/2024 | | A61B 8/465 |

OTHER PUBLICATIONS

Michael O'Riordan; Intracardiac Echo a Good Imaging Option to Guide LAA Closure; Daily News; Feb. 2023; pp. 1-7.

Mohamad Alkhouli; The ICE LAA Study: Another Proof of Concept or a PASS to the Future?; JACC Cardiovascular Interventions; 2023; vol. 16; pp. 652-654.

Extended European Search Report (EESR) mailed Jan. 27, 2026 in counterpart European Patent Application No. 25202367.6.

Morais Pedro et al: "Semiautomatic 1-15 Estimation of Device Size for Left Atrial Appendage Occlusion in 3-D TEE Images", IEEE Transactions on Ultrasonics, Ferroelectrics, and Frequency Control, IEEE, USA, A61B; vol. 66, No. 5; May 1, 2019; pp. 922-992.

* cited by examiner

LEFT ATRIAL APPENDAGE ASSESSMENT METHOD

FIELD

This disclosure relates to medical imaging.

BACKGROUND

The Left Atrial Appendage (LAA) is a small pouch extending off the side of the left atrium in the heart that functions as a decompression chamber when atrial pressure is high. The LAA plays a key role in the thromboembolic risk associated with atrial fibrillation and may also have a possible triggering effect of atrial tachyarrhythmia. Atrial fibrillation (A-fib) is a type of abnormal heart rhythm where the upper chambers of the heart beats irregularly and rapidly, increasing the risk of blood clots forming in the heart. If a blood clot in the left upper chamber (left atrium) breaks free from the heart area, it can travel to the brain and cause a stroke, a leading cause of death. Studies have shown that the LAA is a particularly common site where blood clots form in people with A-fib.

Understanding the morphology and function of LAA is pivotal for the treatment of A-fib. The measurement of the size of the LAA opening has generally been done from cardiac CT or a transesophageal echocardiogram (TEE). There are disadvantages with both CT and TEE. CT is a pre-procedure imaging procedure that uses ionizing radiation. TEE requires general anesthesia and the associated risks and the administration of anesthesia requires the presence of anesthesia staff to be present. In addition, the imaging quality of TEE is often operator dependent.

SUMMARY

By way of introduction, the preferred embodiments described below include methods, systems, instructions, and computer readable media for LAA closure device specification from 2D ICE.

In a first aspect, a method if provided for left atrial appendage (LAA) assessment, the method comprising: acquiring a plurality of images of a left atrium of a patient; generating a model of the left atrium from the plurality of images of the left atrium; acquiring a plurality of images of a LAA of the patient; determining, based on the model, if the plurality of images of the LAA are sufficient to accurately estimate a specification of a LAA closure device; and computing and providing, when the plurality of images of the LAA are sufficient, an anatomical measurement of the LAA or providing, when the plurality of images are not sufficient, instructions for an operator to acquire additional images of the LAA.

In a second aspect a system for left atrial appendage (LAA) device selection is provided, the system comprising: a 2D ICE imaging system configured to acquire left atrium image data of a patient's heart and left atrial appendage image data of the patient's heart; an imaging processor configured to generate a three dimensional model of the left atrium of the patient from the left atrium image data, the imaging processor further configured to register the left atrial appendage image data to the three dimensional model and determine that the left atrial appendage is sufficiently visualized in the left atrial appendage image data; wherein the imaging processor is further configured to compute at least one anatomical measurement of the left atrial appendage and select a device for an left atrial appendage closure procedure based on at the at least one anatomical measurement.

In a third aspect, a non-transitory computer implemented storage medium is provided that stores machine-readable instructions executable by at least one processor for left atrial appendage (LAA) assessment, the machine-readable instructions comprising: acquiring a plurality of images of a left atrium of a patient; generating a model of the left atrium from the plurality of images of the left atrium; acquiring a plurality of images of a LAA of the patient; determining, based on the model, if the plurality of images of the LAA are sufficient to accurately estimate a specification of a LAA closure device; and computing and providing, when the plurality of images of the LAA are sufficient, an anatomical measurement of the LAA or providing, when the plurality of images are not sufficient, instructions for an operator to acquire additional images of the LAA.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Embodiments described herein provide systems and methods for LAA closure device specification from two dimensional (2D) Intracardiac Echo imaging (ICE). In an imaging procedure, 2D ICE is used to acquire images of the left atrium of a patient. A model of the left atrium is generated from the images. The model is used to validate subsequent imaging of the LAA of the patient. Anatomical measurements from the validated subsequent imaging may be used to select or specify a LAA closure device in order to, for example, treat atrial fibrillation patients.

2D ICE is an imaging modality that provides high-resolution real-time visualization of cardiac structures, continuous monitoring of a catheter location within the heart, and early recognition of procedural complications, such as pericardial effusion or thrombus formation. ICE has largely replaced transesophageal echocardiography as the imaging modality for guiding certain procedures, such as atrial septal defect closure and catheter ablation of cardiac arrhythmias, and has an emerging role in others, including mitral valvuloplasty, transcatheter aortic valve replacement, and left atrial appendage closure. The ICE catheter may be augmented with a tracking device such as radio frequency transmitter that makes it possible to determine the location of the catheter when images are acquired.

Figure 1:
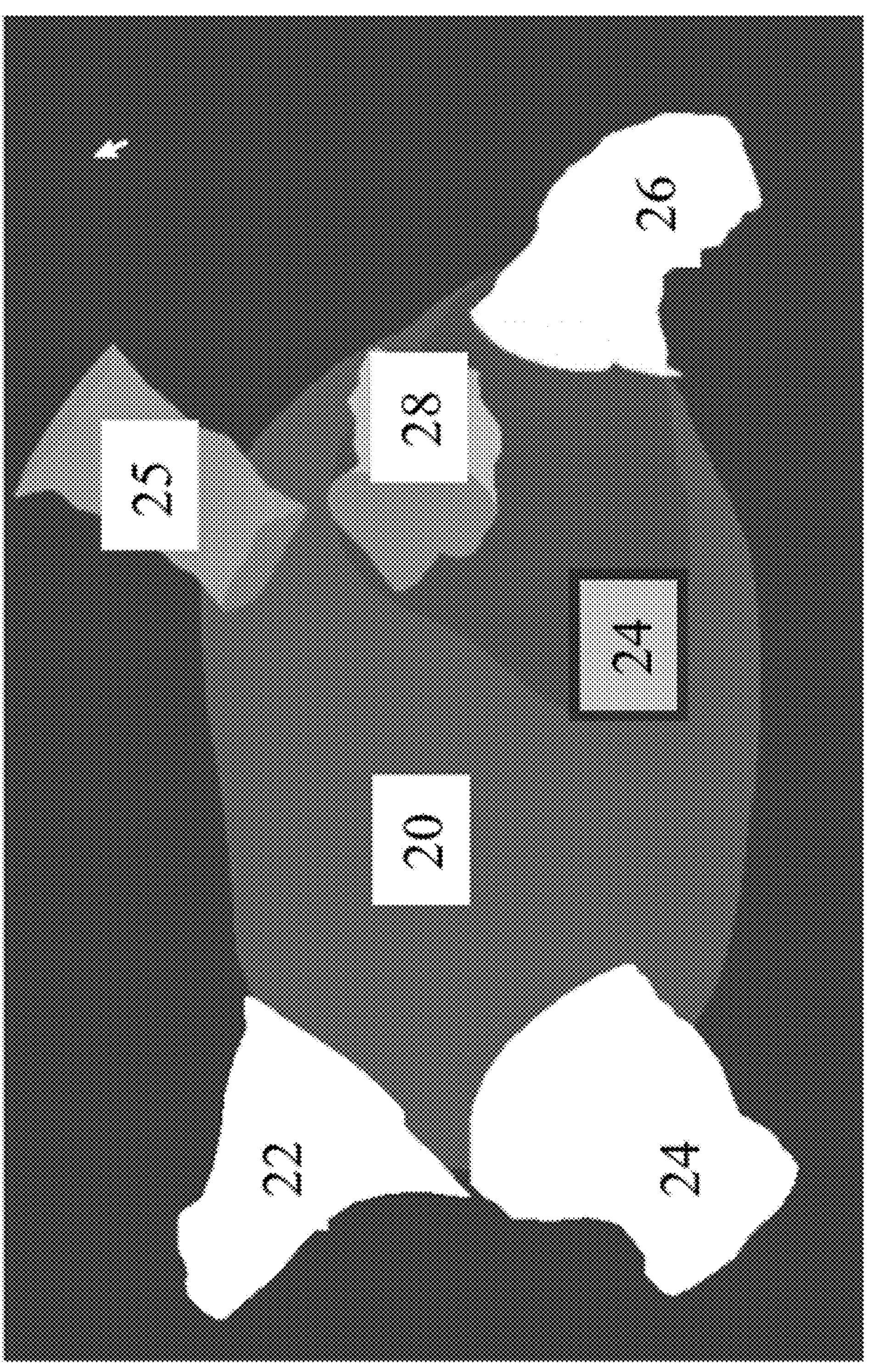
FIG. 1 depicts an example of the components of a heart.

FIG. 1 depicts an example of the different components of a heart of a patient. FIG. 1 depicts an example left atrium 20 and surrounding structure of interest. The structure includes the left atrial appendage (LAA) 26, left inferior pulmonary vein (LIPV) 25, left superior pulmonary vein (LSPV) 28, right inferior pulmonary vein (RIPV) 22, and right superior pulmonary vein (RSPV) 24. The left ventricle or other heart chambers may be an anatomy of interest when performing an ultrasound procedure. While the embodiments described herein focus on the LAA in particular, the methods and systems may be applied to other organs, tissues, or structures that may benefit from real time segmentation and quantification.

As is depicted in FIG. 1, the LAA 26 is located on a side of the pulmonary arteries that bring in blood from the lungs. The position of the LAA 26 can cause blood to pool there instead of flowing into the left ventricle of your heart. For patients with normal heart rhythm, the LAA 26 squeezes rhythmically with the rest of the left atrium. This rhythmic contraction ensures that blood in the pouch is ejected when the left atrium empties into the left ventricle, where it is then pumped all over the body. However, AFib patients experience poor atrial contractions during an episode. These weak contractions, combined with blood pooling, may result in clot formation, which may form in the LAA 26. Anticoagulation therapy is typically used as the main embolism prevention treatment for patients with atrial fibrillation, however, it may have a poor long-term compliance and potential bleeding complications. Left atrial appendage closure (LAAC) is a minimally invasive cardiac intervention to prevent blood clots from forming in LAA 26 by closing it off with a device. This can significantly reduce the risk of stroke in people with A-fib who are at high risk of developing blood clots. It serves as an alternative solution for anticoagulation therapy and is recommended for people with A-fib who cannot take blood-thinning medications.

ICE is increasingly used to guide and provide navigation support during LAAC procedures. For example, the most frequently used imaging for, for example Watchman FLX implants and other LAA 26 implants is ICE. The use of ICE for LAAC has advantages over a TEE-guided approach. The procedure can be carried out under local anesthesia with the patient awake and responsive. The risks and postprocedural discomfort associated with general anesthesia or deeper sedation and endotracheal intubation can be avoided, and the procedure can be carried out in patients contraindicated for general anesthesia and in those with gastroesophageal diseases. An anesthesiology team and a TEE operator are not required, and the procedural turnover time is reduced.

However, there are challenges for using 2D ICE in procedures such as LAAC. One of the principal measurements used in choosing a specific LAAC device is the diameter of the LAA ostia (opening). The size of the ostium varies dramatically in different patents. Measuring the size is an important task when performing LAAC, for example, in order for determining which of several variations of an LAAC device to use for a specific patient. This may be challenging as 2D ICE provides a 2D view of the 3D anatomy of the LAA 26 and many clinical sites have limited experience working with ICE and getting the best images. Although the LAA ostia may be seen in a particular ICE image frame it may not show the full extent of the LAA ostia diameter. From a single image frame or from a series of image frames it may not be obvious that the full diameter has not been fully seen.

Figure 2:
FIG. 2 depicts an example of an ICE image of the LA and the LAA of a patient.
Figure 3B:
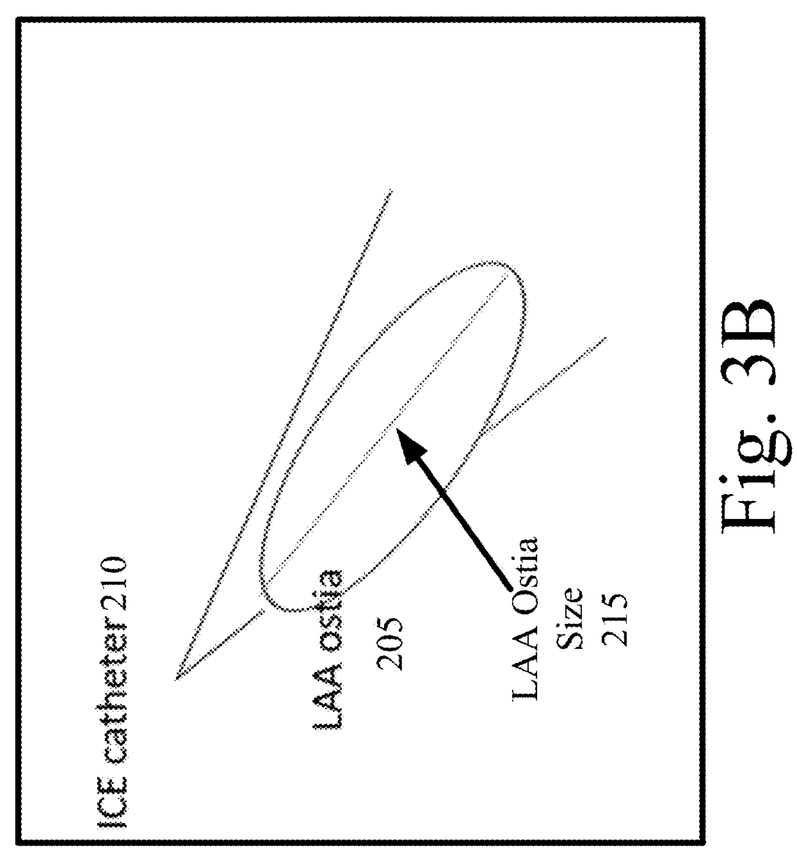
FIGS. 3A and 3B depict examples of different orientations of an ICE catheter and different scan planes.
Figure 3A:
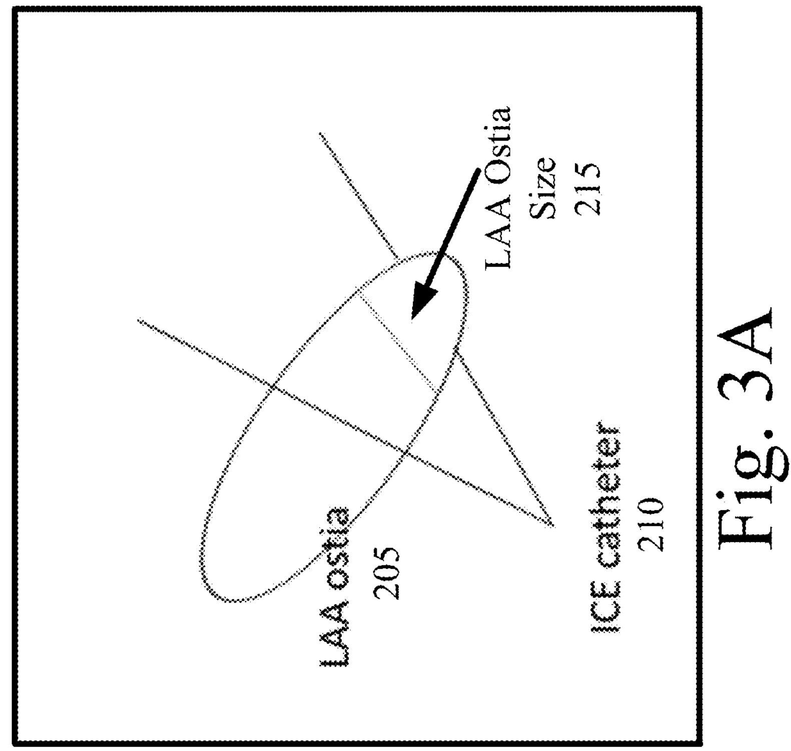

FIG. 2 depicts an example of a 2D ICE image of a LAA 26. In the 2D image both the LA 20 and the LAA 26 of a patient are included. While the location of the LAA 26 may be easy to ascertain, it may not be clear if the 2D image includes a full view of the LAA 26 or just a portion. FIG. 3 depicts an example of how different scan planes may result in different views and depictions of the LAA 26, and in particular the depicted size of the LAA ostia 205. FIG. 3 depicts two different scenarios where an ICE catheter 210 is used to image an LAA ostia 205 represented as an oval. The ICE image frame is shown as a wedge representing the ultrasound fan of image information. The diameter of the LAA ostia 205 as measured (LAA Ostia Size 215) is depicted in the ICE image frame. The diameter in FIG. 3A underestimates the maximum diameter of the LAA ostia 205. The diameter in FIG. 3B is an accurate estimate of the maximum diameter (LAA Ostia Size 215) of the LAA ostia 205. As shown, if the operator incorrectly positions the catheter, the resulting measurement may be off by a significant amount. Due to the limitations of two-dimensional (2D) ICE and the difficulty in manual manipulation of the ICE transducer, the LAA ostia 205 and other three-dimensional (3D) anatomical structures may not be sufficiently observed in certain views. This introduces difficulties to electrophysiologists as well as echocardiography image analysis algorithms.

Embodiments provide mechanisms to verify or validate that the acquired image is sufficient for specifying a LAAC device. In an embodiment, an estimated model of the LA anatomy including the LAA 26 and the known position of a 2D ICE frame relative to that model is used to check that the full diameter of the LAA ostia 205 has been seen. Any uncertainty in the model and in the ICE image frame position may be used in an estimate of the probability that the LAA ostia 205 diameter has been measured up to a certain confidence. If the LAA ostia 205 diameter has not been confidently seen, then based on the model the system may suggest which way to move the ICE catheter 210 to get a better estimate of the LAA ostia 205 diameter. For instance, shifting the catheter forwards or rotating the catheter ("clocking"). Simulating alternative views from the LA model that the ICE catheter 210 might reach may allow for the simulated calculation of the LAA ostia 205 diameter. All distinct such views may be calculated and the best view reported to the user in the form of guidance to move the ICE catheter 210 so as to obtain the best view.

Whether or not an image is sufficient for estimating the size of the LAA for an LAAC device depends on the specific closure device and the device manufacturer's recommendations for the deployment of the device. A device manufacturer may specify several measurements that need to be made in choosing which closure device should be used for a patient. For example, a device manufacturer may require that the diameter of the LAAC opening be measured with an accuracy of 2 mm. An image would be sufficient if it shows a diameter of the LAA that is within 2 mm of the actual diameter of the LAA. Since there may be some uncertainty in the model recovered from the ICE images, the diameter measured from the model may only be known with a 90% accuracy. In an example, the system outputs that the current image is sufficient with a 90% probability given that the diameter seen on an image is within 2 mm of the maximum diameter as measured on the model.

Figure 4:
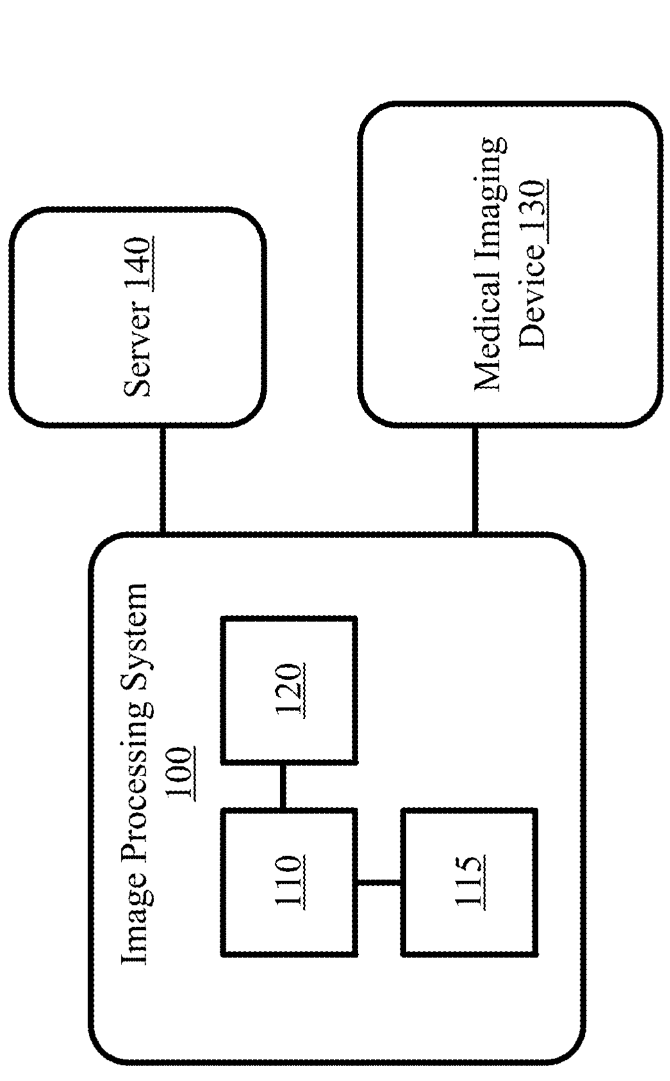
FIG. 4 depicts an example system for LAA closure device specification from 2D ICE according to an embodiment.

FIG. 4 depicts an ultrasound system 100 for LAAC device specification from 2D ICE. The system includes an image processing system 100, a medical imaging device 130, and optionally a server 140. The server 140 may be configured to perform any of the tasks of the image processing system 100 including processing and/or storing of the data and models. The server 140 may be or include a cloud-based platform. The image processing system 100 includes a processor 110 (imaging processor 110), a memory 120, and a display 115. The image processing system 100 may be included with or coupled to the medical imaging device 130. The image processing system 100 is configured to generate a model of the LA using acquired 2D ICE images of the LA. The image processing system 100 is configured to, using the model, verify that 2D ICE images of the LAC are sufficient to specify a LAAC device for the patient. In an example, images of the LAC that are not acquired using an appropriate orientation/scan plane may be rejected as these images are not sufficient to accurately measure the LA ostia. Sufficiently, for example, may mean that at least 80, 90, 95% of the LAA/LA ostia are visible in at least one image so that an accurate assessment may be performed. The image processing system 100 may also be configured to train or store a machine learned model for these tasks. The imaging data is acquired from the medical imaging device 130 in real time for example as an ultrasound sequence. Additional, different, or fewer components may be provided. For example, a computer network is included for remote processing of locally captured ultrasound data, for example by the server 140. As another example, a user input device (e.g., keyboard, buttons, sliders, dials, trackball, mouse, or other device) is provided for user alteration or placement of one or more markers. In yet another example, one or more devices or components used in a medical procedure such as left atrial appendage closure (LAAC) may be included. For example, devices that block the left atrial appendage's opening to keep blood clots that form in the LAA 26 from going into the bloodstream, devices that clamp the base of the LAA 26 to close it off, or devices that use a band or suture loop to close off the LAA 26 among other medical devices.

The medical imaging device 130 may be an ultrasound system 130 configured to acquire scan planes of the LA and the LAA 26. Ultrasound imaging uses sound waves to image internal body structures. Different ultrasound procedures include transthoracic echocardiogram (TTE), transesophageal echocardiogram (TEE), and Intracardiac Ultrasound (ICE) among others. TTE is a non-invasive procedure where a transducer (or probe) is placed on the chest of the patient. Images are recorded using ultrasound data. For TEE, the probe is passed through a patient's esophagus in order to be near the patient's heart. The probe may have an ultrasound transducer at the tip in order to provide imaging capabilities. ICE uses a ultrasound-tipped catheter where the catheter is threaded thru a vein in the groin and up into the heart. ICE may be used to produce detailed images of the heart's size, structure, and function, as well as detailed images of the heart's valves. The context of use as described herein is for treatment of atrial fibrillation under the guidance of ICE imaging although other procedures and ultrasound techniques may be used. The left atrium may be the most common anatomy of interest for this context. The left ventricle or other heart chambers may be the anatomy of interest in other embodiments. Other ICE imaging locations may result in other anatomy of interest, such as arteries or veins. The left atrium and the corresponding anatomy are used as examples below. In an embodiment, for a LAAC procedure, the catheter is introduced via a femoral venous access and placed either in the right atrium, the right ventricular outflow tract, coronary sinus, or the left atrium. The medical imaging device 130 is configured to acquire 2D scan planes of the left atrium and the LAA 26.

The processor 110 is a general processor, digital signal processor, graphics processing unit, application specific integrated circuit, field programmable gate array, artificial intelligence processor, digital circuit, analog circuit, combinations thereof, or other now known or later developed device for LAAC device specification from 2D ICE images, among other processes described below. The processor 110 is a single device, a plurality of devices, or a network. For more than one device, parallel or sequential division of processing may be used. Different devices making up the processor 110 may perform different functions. In one embodiment, the processor 110 is a control processor or other processor of the medical imaging device 130. In other embodiments, the processor 110 is part of a separate workstation or computer. The processor 110 operates pursuant to stored instructions to perform various acts described herein. The processor 110 is configured by software, design, firmware, and/or hardware to perform any or all of the acts of FIGS. 5 and 7 and any other computations described herein.

Figure 5:
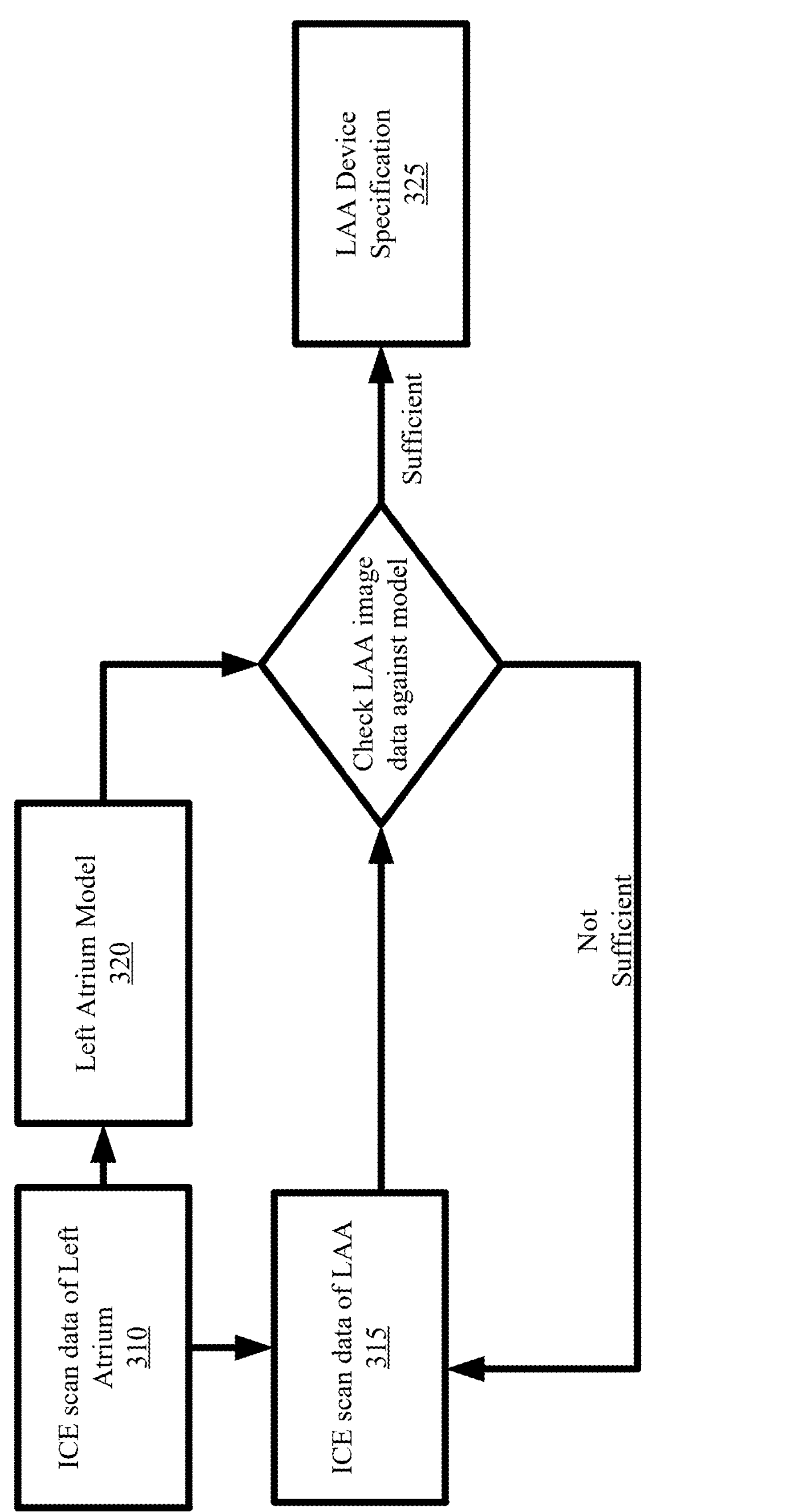
FIG. 5 depicts an example workflow for LAA closure device specification from 2D ICE according to an embodiment.

FIG. 5 depicts a workflow for LAA closure device specification from 2D ICE according to an embodiment. A patient may be prepared for the procedure. ICE uses a ultrasound-tipped catheter where the catheter is threaded through a vein in the groin and up into the heart. An ICE overview 310 of the left atrium is acquired. The left atrium is modeled generating a Left Atrium Model 320. ICE imaging of the LAA 26 is performed to acquired ICE scan data of the LAA 315. The ICE measurements of the ICE imaging of the LAA 26 are checked against the model. If the measurements are acceptable, a LAAC device is selected/specified based on the measurements and an LAA device specification 325 and the procedure is performed. If the measurements are not acceptable, the operator is notified and additional imaging of the LAA 26 is performed.

The processor 110 is configured to generate a model of the LA of the patient from images acquired by the medical imaging device 130. The processor 110 is configured to use the model to determine if acquired images of the LAA 26 are sufficient to specify a device for a LAAC procedure. The processor 110 may be further configured to use the model to validate measurements from subsequent images acquired by the medical imaging device 130 of the LAA 26. Validation, may for example, include determining an orientation of the scan plane and whether or not an acceptable view of the ostium is present.

In an embodiment, the processor 110 is configured to generate a 3D model of the left atrium by combining multiple scan planes acquired by the medical imaging device 130. In an ICE imaging procedure, a sensor provides a position/orientation of the scan planes. The known locations provided are used to populate a volume with data from the scan planes. The position of the catheter may be identified from, for example, a magnetic position sensor. The location and orientation of the catheter/transduce define the scan plane. Different scan planes have different positions/orientations. The sensed positions are used to assign scalar or other ultrasound data to different voxels in the 3D volume. Alternatively, the sensed positions are used to align the planar locations represented by the ultrasound data within the volume. The ultrasound data is mapped to three dimensions using the positions of the scan planes.

Figure 6B:
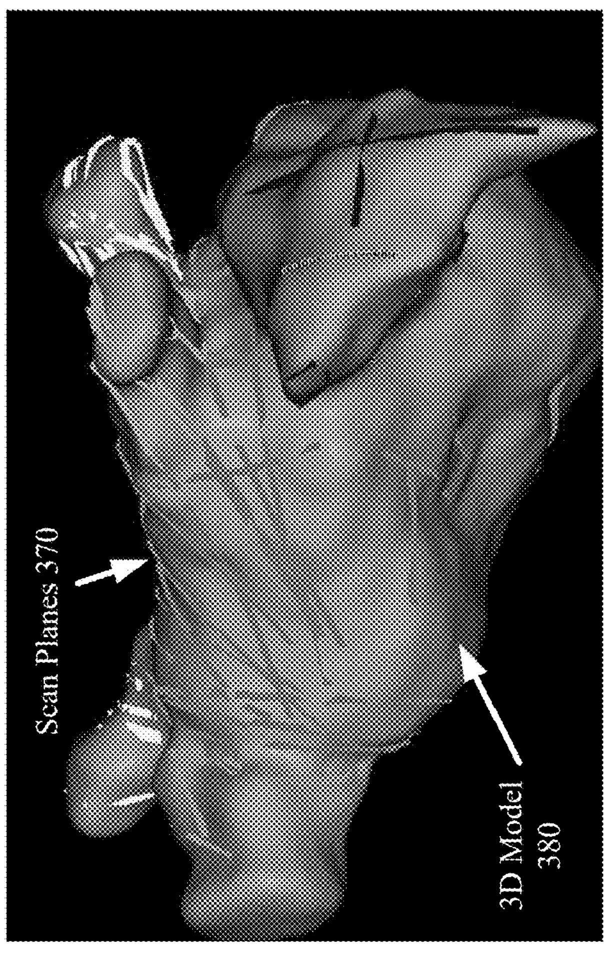
FIGS. 6A and 6B depict 2D ICE scan planes and a 3D model of a heart according to an embodiment.
Figure 6A:
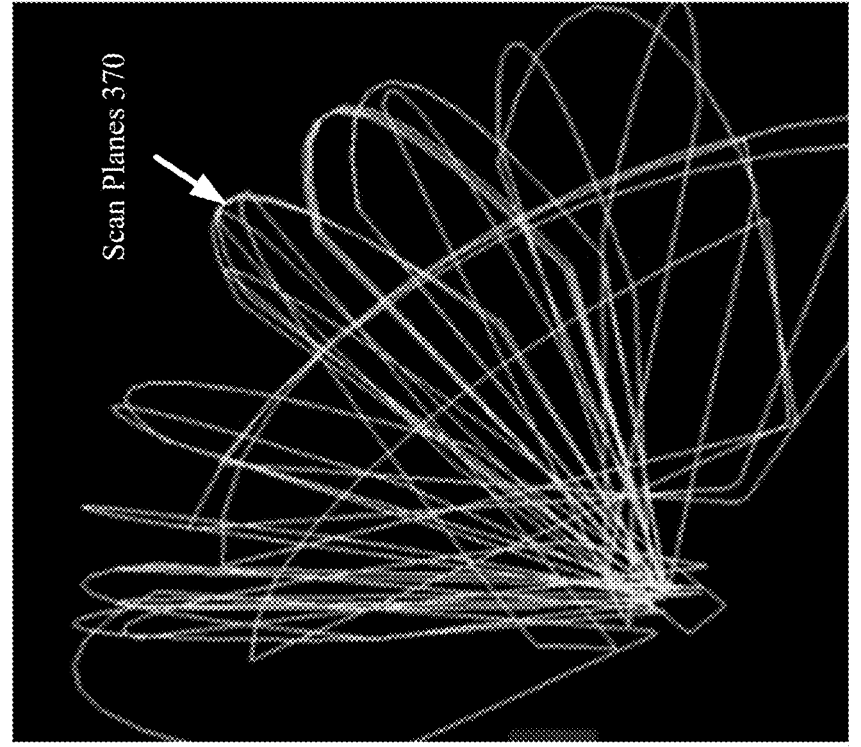

FIG. 6A depicts an example of different scan plans 370 overlaid on a 3D environment. When the catheter/transducer is rotated to different orientations, different scan planes are captured. When the data from some or all of the scan planes 370 is combined, a 3D view may be visualized. The 3D view may be sparse, e.g., missing some data between the scan planes. The 3D view, however, may include sufficient data to generate a mesh, and/or allow the system to identify the locations of each scan plane 370 relative to one another and any landmarks or features of the heart. FIG. 6B depicts an example model 380 generated by combining the different scan planes, segmenting the data, generating a mesh model, and adding in some appearance data to flesh out the model. In both 6A and 6B, the scan planes 370 are visible.

In an embodiment, the processor 110 is configured to perform segmentation of the acquired images to generate the LA model, for example using a machine trained model. Different types of models or networks may be trained and used for the segmentation task. Segmentation divides an image into areas based on a specified description, such as segmenting body organs/tissue. In an embodiment for a segmented volume, the segmented data includes a plurality of pixels. Each pixel represents a two-dimensional display element. For example, a pixel represents a quantity of 2D data. For the segmentation, landmark detection, and tracking, the processor 110 may apply one or more trained machine learned networks or models that have been trained for the respective task.

The machine learned network(s) or model(s) may include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to the next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes.

The segmented data may be used to form a mesh model of the LA of the patient. An algorithm may be used to compute a graphical mesh representation from an image segmentation. Features such as landmarks/tissues/contours/boundaries etc. may be identified and labeled in the segmented data/3D model. These features may be used to determine if newly acquired ultrasound data of the LA is acquired at an acceptable angle/orientation.

Image data, the machine trained networks, training data, computed metrics, and other data may be stored in the memory 120. The memory 120 may be or include an external storage device, RAM, ROM, database, and/or a local memory (e.g., solid state drive or hard drive). The same or different non-transitory computer readable media may be used for the instructions and other data. The memory 120 may be implemented using a database management system (DBMS) and residing on a memory 120, such as a hard disk, RAM, or removable media. Alternatively, the memory 120 is internal to the processor 110 (e.g., cache). The instructions for implementing the processes, methods, and/or techniques discussed herein are provided on non-transitory computer-readable storage media or memories, such as a cache, buffer, RAM, removable media, hard drive, or other computer readable storage media (e.g., the memory 120). The instructions are executable by the processor 110 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor 110 or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The processor 110 is configured to determine if subsequent image data of the LAA 26 is sufficient to use when specifying a LAAC device. To determine if the image data of the LAA 26 is sufficient, the processor 110 may register the image slice of the LAA 26 to the heart model and then determine its orientation. For example, a view of the LA from a particular scan plane may be acquired at an orientation that is offset by 5, 10, 20 degrees from optimal. The offset angle makes it difficult to properly assess the LA ostia. The processor 110 is configured to determine that the newly acquired image data of the LA is not sufficient by matching features of the newly acquired image to the 3D model and deriving where the scan plane slices through the heart region.

The processor 110 is further configured to check/validate various measurements from ICE imaging of the LAA 26 against the LA model. In an embodiment, the processor 110 is configured to measure features of the LAA 26 and validate the measurements based at least in part on the heart model. The processor 110 may determine and use the orientation of the catheter/scan plane and an algorithm to determine if a measurement of the patient's LA ostia is within a predefined range of an estimated LA ostia measurement that is derived from the heart model. The algorithm is then used to determine if the ICE images of the LAA 26 are sufficient to accurately estimate the needs of the LAA closure device for this patient based on the ICE images of the LAA 26 and the model of the LA. If the ICE images of the LAA 26 are not sufficient then the users of the system are notified of this and may be told how to acquire additional appropriate images to better determine the patient's specific needs for an LAA closure device. If the ICE images are sufficient, then the processor 110 may be further configured to select a device for a LAAC procedure based on the LAA 26 measurements.

The display 115 is configured to display or otherwise provide the images and measurements of the patient to the user. The display may be configured to display the 3D model, acquired 2D ICE images, and an overlay of the 2D ICE images of the LAA 26 and the 3D model. In an example, the scan plane of the acquired LAA 2D ICE images may be displayed to an operator so that the operator may understand why the images are not sufficient, for example, how offset the scan plane is from an optimal or useful scan plane. The display 115 is a CRT, LCD, projector, plasma, printer, tablet, smart phone or other now known or later developed display device for displaying the output.

In an embodiment, the system is configured to measure not only the LAA diameter but any measurement of the size or shape of the LAA 26 that is used in choosing a device for an LAA 26 closure. Many manufacturers of LAA closure devices provide solutions that vary in size. If the only selection among devices is based on the size then this is referred to as "sizing" the device. The system may be used to aid in sizing or in choosing between different manufacturers devices if anatomical measurements are used in the selection among the different available devices.

In an embodiment, the system may detect if the LAA 26 is visible in an ICE frame. The system further registers an ICE frame with a model of the left atrium anatomy and estimates the variability in the alignment of the ICE frame with the anatomical model. The system if further configured to reason based on uncertainty in the ICE frame alignment and uncertainty in the anatomical model to determine the uncertainty in specific measurements such as LAA ostia 205 diameter. The system relieves the need for pre-procedure CT imaging, TEE imaging, or other imaging distinct from the ICE that can be used as guidance during the LAA closure procedure. The system provides a measure of the confidence with which the LAA 26 has been measured for sizing an LAA closure device from ICE. In addition, the system provides instructions on how to better position the ICE catheter 210 in order to get an ICE image that will better support measurements of the LAA 26 useful for choosing an LAA closure device.

Figure 7:
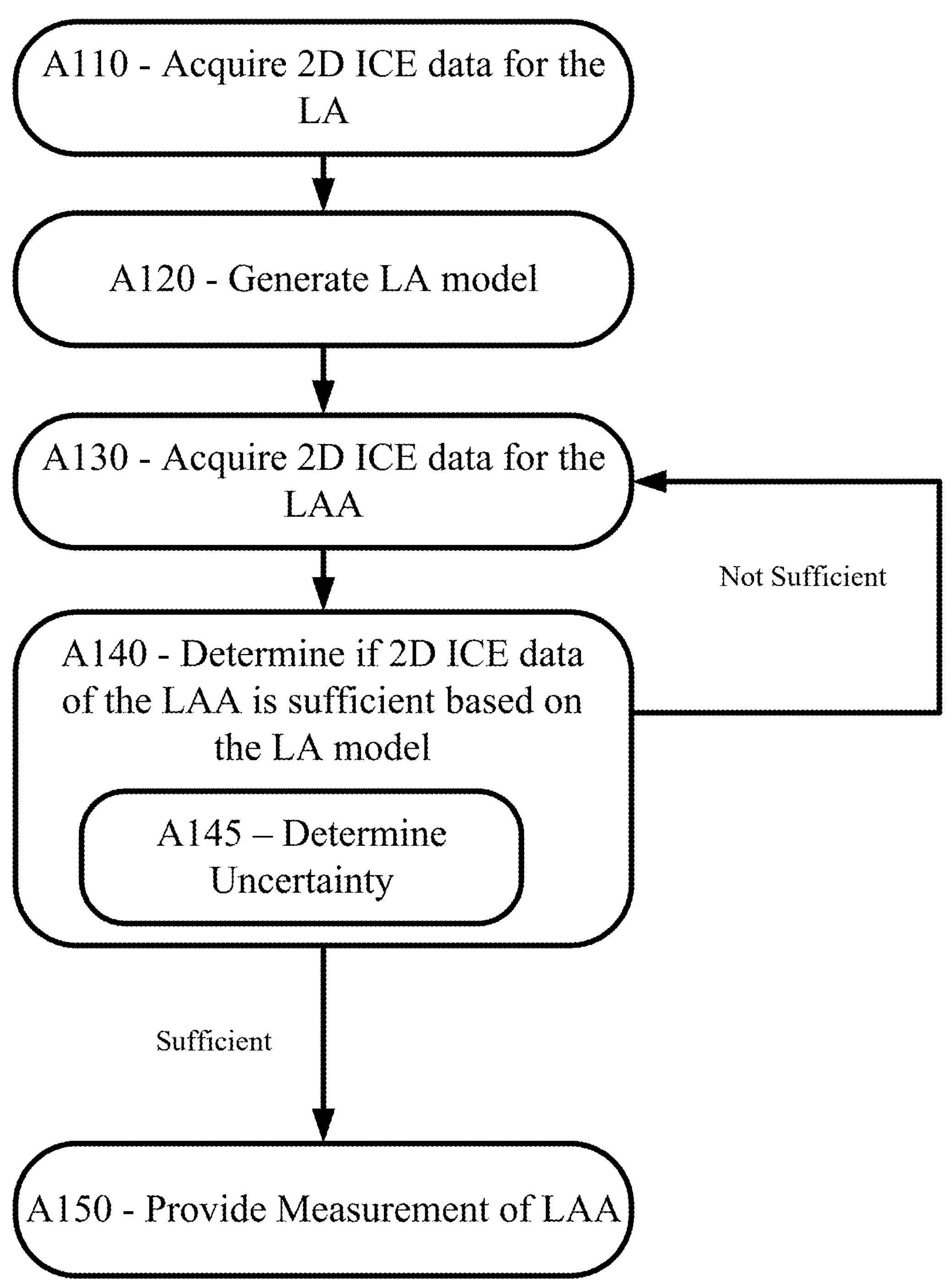
FIG. 7 depicts a method for LAA closure device specification from 2D ICE according to an embodiment.

FIG. 7 depicts an example method using an estimated model of the anatomy to guide 2D ICE imaging of the LAA ostia 205 to best choose a device for the LAA closure. The acts are performed by the system of FIGS. 4, 5, 8, 9 other systems, a workstation, a computer, and/or a server. Additional, different, or fewer acts may be provided. The acts are performed in the order shown (e.g., top to bottom) or other orders. Certain acts may be omitted or changed depending on the results of the previous acts and the status of the patient.

At Act A110, a plurality of images of a left atrium of a patient are acquired. The ultrasound scanner uses an ICE catheter 210 to image. The transducer of the ICE catheter 210 scans a plane. The scan plane is oriented based on a position of the catheter. As the catheter moves (e.g., translates or rotates), different scan planes are scanned. Each scan generates a frame of data representing the scan plane at that time. The frame of ultrasound data may be scalar values or display values (e.g., RGB) in a polar coordinate or Cartesian coordinate format. The frame of ultrasound data may be a B-mode, color flow, or other ultrasound image. A sequence of frames of data result from the ICE imaging. Each frame represents a 2D scan plane, so a collection of frames representing different 2D scan planes in the volume of and/or around the heart are acquired.

At Act A120, a model of the left atrium is generated from the plurality of images of the left atrium. The model is generated by combining multiple slices of the left atrium and registering the slices to a common coordinate system using the known positions of the catheter/transducer. An example of the scan planes (slices) and how they may be combined to generate a model is provided in FIGS. 6A and 6B. The known locations represented by the ultrasound data (plurality of images) are used to populate a volume. The sensed positions are used to assign scalar or other ultrasound data to different voxels. Alternatively, the sensed positions are used to align the planar locations represented by the ultrasound data within the volume. The ultrasound data is mapped to three dimensions using the positions of the scan planes. The mapping forms a 3D sparse ICE volume using the location information associated with each ICE image. A set of 2D ICE images are input, each including part of the heart in its field of view. The sensed 3D position is used to map all the 2D ICE images to 3D space, thus forming a sparse ICE volume. The generated 3D sparse ICE volume keeps the spatial relationships among individual ICE views.

In an embodiment, the model is segmented using a machine learned network. The 3D segmentation is a labeling by voxel or location of different anatomy. The anatomy represented by each location is labeled. Alternatively, the segmentation forms a 3D mesh for each anatomy. Other segmentation results may be provided. The 3D segmentation provides a boundary for one or more structures in 3D. The segmentation is of one or more structures of interest, such as identifying the locations of a sub-set or all the anatomical structures of interest, for example different.

In an embodiment, the processor 110 generates a 3D segmentation from input of the ICE volume to a machine-learned network. The 3D segmentation is a labeling by voxel or location of different anatomy. The anatomy represented by each location is labeled. Alternatively, the segmentation forms a 3D mesh for each anatomy. Other segmentation results may be provided. The 3D segmentation provides a boundary for one or more structures in 3D. The segmentation is of one or more structures of interest, such as identifying the locations of a subset or all the anatomical structures of interest for the left atrium such as, for example leaflets of the heart valves (tricuspid, aortic, mitral), segments of each heart chamber, proximal portions of arteries and veins attached to the heart. The feature data/identified landmarks may be used to register newly acquired images to the 3D heart model.

In an embodiment, the 3D segmentation uses a machine-learned network. The ICE volume and/or plurality of 2D slices with or without other data are input to the machine-learned network and a 3D segmentation is output in response. The machine-learned network may further be configured to fill in portion of the 3D volume that arise due to the lack of data from a limited number of 2D slices. An example is provided in U.S. Pat. No. 11,534,136B2 herein incorporated by reference in its entirety.

Machine learning for image segmentation may be done by extracting a selection of features from input images. These features may include, for example, pixel gray levels, pixel locations, image moments, information about a pixel's neighborhood, etc. A vector of image features is then fed into a learned classifier which classifies each pixel of the image into a class. The parameters of the classifier are learned automatically by giving the classifier input images for which the ground truth classification results is known. The output of the model can then be compared to the ground truth, and the parameters of the model are adjusted so that the model's output better matches the ground truth value. This procedure is repeated for a large amount of input images, so that the learned parameters generalize to new, unseen examples. The process of adjusting the model's parameters is referred to as training. Deep learning may also be used for segmentation, for example using a neural network. Deep learning-based image segmentation may be done, for example, using a convolutional neural network (CNN). Convolutional neural networks have a layered structure where series of convolutions are performed on an input image. Kernels of the convolutions are learned during training. The convolution results are then combined using a learned statistical model that outputs a segmented image.

The machine-learned network may be an image-to-image network, such as a fully convolutional U-net trained to convert the ICE volume to the 3D segmentation. For example, the trained convolution units, weights, links, and/or other characteristics of the network are applied to the data of the ICE volume and/or derived feature values to extract the corresponding features through a plurality of layers and output the 3D segmentation. The features of the input are extracted from the ICE images as arranged in 3D. Other more abstract features may be extracted from those extracted features using the architecture. Depending on the number and/or arrangement of units or layers, other features are extracted from the input. The network includes an encoder (convolutional) network and decoder (transposed-convolutional) network forming a "U" shape with a connection between passing features at a greatest level of compression or abstractness from the encoder to the decoder. Skip connections may be provided. Any now known or later developed U-Net architectures may be used. Other fully convolutional networks may be used. In one embodiment, the network is a U-Net with one or more skip connections. The skip connections pass features from the encoder to the decoder at other levels of abstraction or resolution than the most abstract (i.e. other than the bottleneck). Skip connections provide more information to the decoding layers. A fully convolutional layer may be at the bottleneck of the network (i.e., between the encoder and decoder at a most abstract level of layers). The fully connected layer may make sure as much information as possible is encoded. Batch normalization may be added to stabilize the training.

For training any of the networks, various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation are not used, but may be (e.g., using batch normalization and dropout). During the optimization, different distinguishing features are learned. The features providing an indication of anatomy location or missing volume information given a input sparse ICE volume are learned. The network minimizes an error or loss, such as the Mean Squared Error (MSE), Huber loss, L1 loss, or L2 loss. In one embodiment, the machine training uses a combination of an adversarial loss (for example using a GAN) and a reconstruction loss. A discriminator of the GAN provides adversarial losses for the segmentation and/or a volume completion. The reconstruction loss is a measure of difference of the 3D segmentation from the ground truth segmentation and of difference of the complete volume from the ground truth volume.

Figure 8:
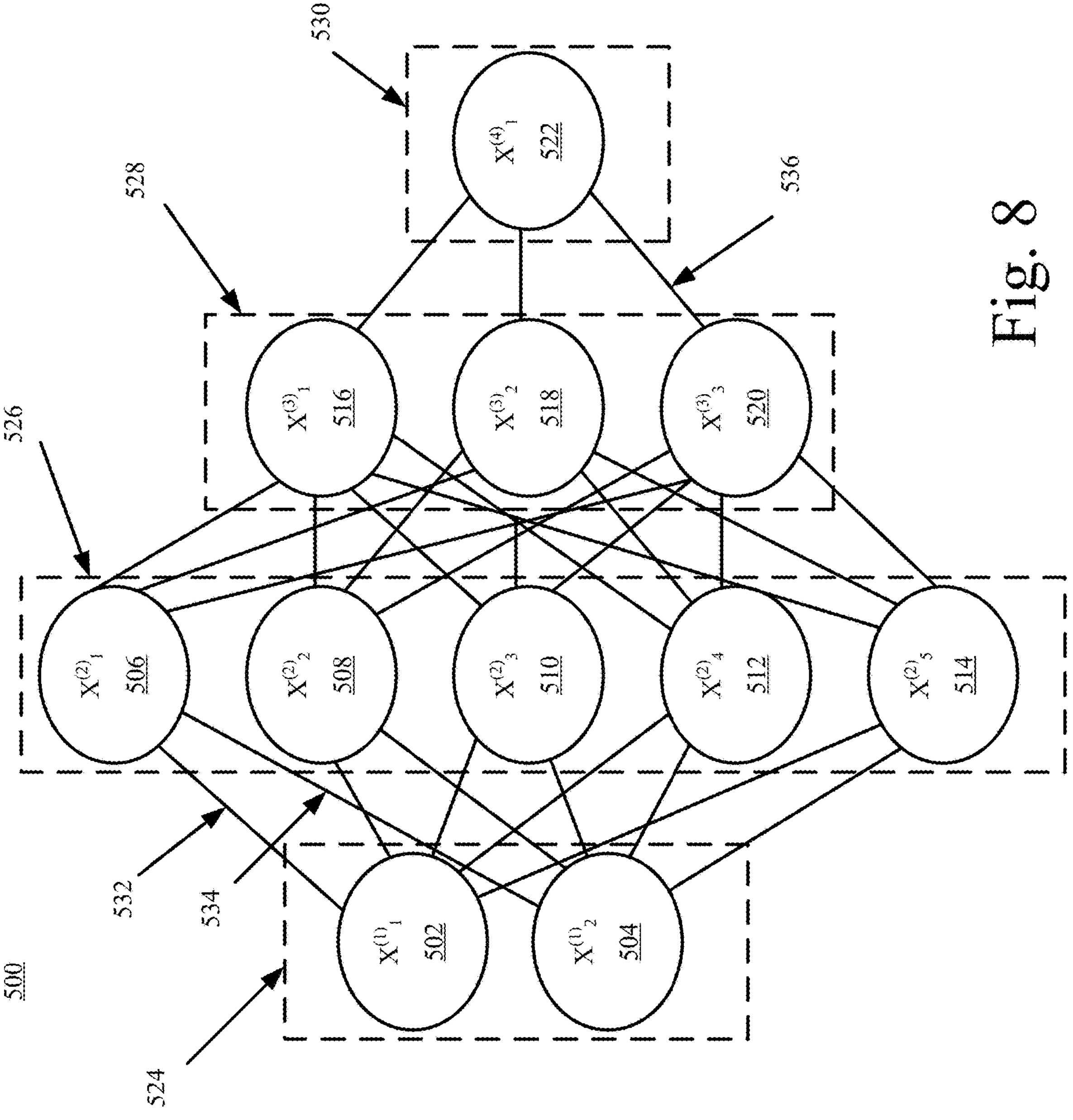
FIG. 8 depicts an example artificial neural network

FIG. 8 shows an embodiment of an artificial neural network 500, in accordance with one or more embodiments. Alternative terms for "artificial neural network" are "neural network", "artificial neural net" or "neural net". The artificial neural network 500 may be used in part in, for example, the one or more machine learning based networks utilized for segmentation, rendering, etc.

The artificial neural network 500 includes nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522, it is also possible that the first node 502-522 and the second node 502-522 are identical. In FIG. 8, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 may be arranged in layers 524-530, wherein the layers may include an intrinsic order introduced by the edges 532, 534, . . . , 536 between the nodes 502-522. In particular, edges 532, 534, . . . , 536 may exist only between neighboring layers of nodes. In the embodiment shown in FIG. 8, there is an input layer 524 including only nodes 502 and 504 without an incoming edge, an output layer 530 including only node 522 without outgoing edges, and hidden layers 526, 528 in-between the input layer 524 and the output layer 530. In general, the number of hidden layers 526, 528 may be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number may be assigned as a value to every node 502-522 of the neural network 500. Here, $$x_i^{(n)}$$

denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 may include a weight being a real number, in particular, the weight is a real number within the interval [—1, 1] or within the interval [0, 1]. Here, $$w_{i,j}^{(m,n)}$$

denotes the weight of the edge between the i-th node 502-522 of the m-th layer 524-530 and the j-th node 502-522 of the n-th layer 524-530. Furthermore, the abbreviation $$w_{i,j}^{(n)}$$

is defined for the weight $$w_{i,j}^{(n,n+1)}.$$

In particular, to calculate the output values of the neural network 500, the input values are propagated through the neural network. In particular, the values of the nodes 502-522 of the (n+1)-th layer 524-530 may be calculated based on the values of the nodes 502-522 of the n-th layer 524-530 by $$x_j^{(n+1)} = f\left(\sum_i x_i^{(n)} \cdot w_{i,j}^{(n)}\right).$$

Herein, the function f is a transfer function (another term is “activation function”). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 524 are given by the input of the neural network 500, wherein values of the first hidden layer 526 may be calculated based on the values of the input layer 524 of the neural network, wherein values of the second hidden layer 528 may be calculated based in the values of the first hidden layer 526, etc.

In order to set the values $$w_{i,j}^{(m,n)}$$

for the edges, the neural network 500 has to be trained using training data. In particular, training data includes training input data and training output data (denoted as $t_i$). For a training step, the neural network 500 is applied to the training input data to generate calculated output data. In particular, the training data and the calculated output data include a number of values, said number being equal with the number of nodes of the output layer.

In particular, a comparison between the calculated output data and the training data is used to recursively adapt the weights within the neural network 500 (backpropagation algorithm). In particular, the weights are changed according to $$w_{i,j}^{\prime(n)} = w_{i,j}^{(n)} - \gamma \cdot \delta_j^{(n)} \cdot x_i^{(n)}$$

wherein $\gamma$ is a learning rate, and the numbers $$\delta_j^{(n)}$$

may be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}{}_j$, if the (n+1)-th layer is not the output layer, and $$\delta_j^{(n)} = \left(x_k^{(n+1)} - ty_j^{(n+1)}\right) \cdot f'\left(\sum_i x_i^{(n)} \cdot w_{i,j}^{(n)}\right)$$

if the (n+1)-th layer is the output layer 530, wherein f' is the first derivative of the activation function, and $$y_j^{(n+1)}$$

is the comparison training value for the j-th node of the output layer 530.

Figure 9:
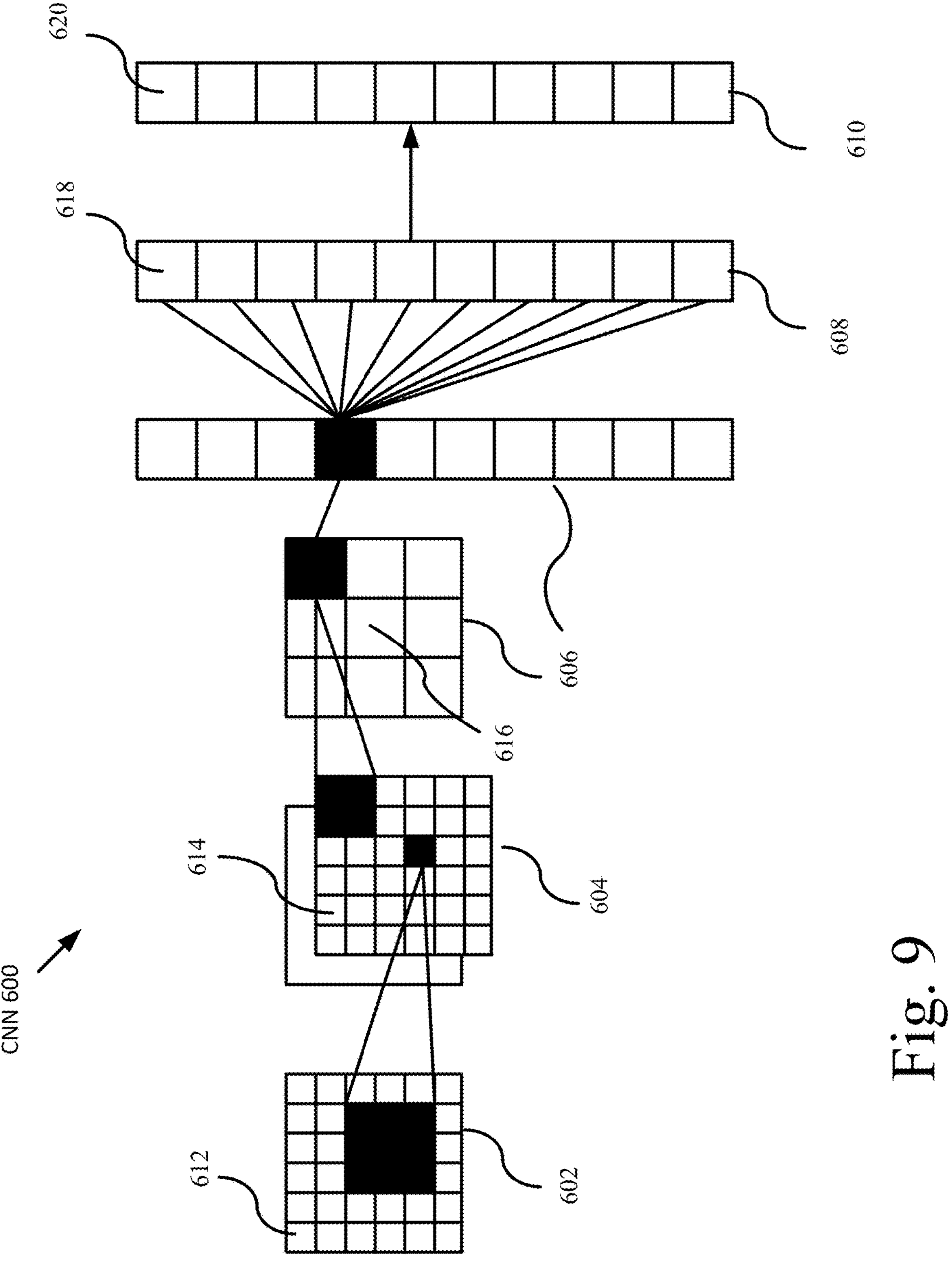
FIG. 9 depicts an example convolutional neural network.

FIG. 9 shows a convolutional neural network 600, in accordance with one or more embodiments. Machine learning networks described herein, such as, e.g., for the segmentation, model generation, rendering, etc. may be implemented using the convolutional neural network 600.

In the embodiment shown in FIG. 9, the convolutional neural network 600 includes an input layer 602, a convolutional layer 604, a pooling layer 606, a fully connected layer 608, and an output layer 610. Alternatively, the convolutional neural network 600 may include several convolutional layers 604, several pooling layers 606, and several fully connected layers 608, as well as other types of layers. The order of the layers may be chosen arbitrarily, usually fully connected layers 608 are used as the last layers before the output layer 610.

In particular, within a convolutional neural network 600, the nodes 612-620 of one layer 602-610 may be considered to be arranged as a d-dimensional matrix or as a d-dimensional image. In particular, in the two-dimensional case the value of the node 612-620 indexed with i and j in the n-th layer 602-610 may be denoted as $$x_{[i,j]}^{(n)}.$$

However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $$x_k^{(n)}$$

of the nodes 614 of the convolutional layer 604 are calculated as a convolution $$x_k^{(n)} = K_k * x^{(n-1)}$$

based on the values $x^{(n-1)}$ of the nodes 612 of the preceding layer 602, where the convolution * is defined in the two-dimensional case as:

$$x_k^{(n)}[i, j] = (K_k * x^{(n-1)})[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels may be interpreted as adding a further dimension (denoted as "depth" dimension), so that the nodes 614 of the convolutional layer 604 are arranged as a (d+1)-dimensional matrix. If the nodes 612 of the preceding layer 602 are already arranged as a (d+1)-dimensional matrix including a depth dimension, using a plurality of kernels may be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data may exploited by enforcing a local connectivity pattern between nodes of adjacent layers, in particular by each node being connected to only a small region of the nodes of the preceding layer.

In embodiment shown in FIG. 9, the input layer 602 includes 36 nodes 612, arranged as a two-dimensional 6×6 matrix. The convolutional layer 604 includes 72 nodes 614, arranged as two two-dimensional 6×6 matrices, each of the two matrices being the result of a convolution of the values of the input layer with a kernel. Equivalently, the nodes 614 of the convolutional layer 604 may be interpreted as arranged as a three-dimensional 6×6×2 matrix, wherein the last dimension is the depth dimension.

A pooling layer 606 may be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 may be calculated based on the values $x^{(n-1)}$ of the nodes 614 of the preceding layer 604 as $$x^{(n)}[i, j] = f(x^{(n-1)}[id_1, jd_2], \ldots , x^{(n-1)}[id_1 + d_1 - 1, jd_2 + d_2 - 1])$$

In other words, by using a pooling layer 606, the number of nodes 614, 616 may be reduced, by replacing a number d1·d2 of neighboring nodes 614 in the preceding layer 604 with a single node 616 being calculated as a function of the values of said number of neighboring nodes in the pooling layer. In particular, the pooling function f may be the max-function, the average, or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 9, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 may be characterized by the fact that a majority, in particular, all edges between nodes 616 of the previous layer 606 and the nodes 618 of the fully-connected layer 608 are present, and wherein the weight of each of the edges may be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 may differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 may also include a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks may be wired using summation (residual/dense neural networks), element-wise multiplication (attention) or other differentiable operators. Therefore, the convolutional neural network architecture may be nested rather than being sequential if the whole pipeline is differentiable.

In particular, convolutional neural networks 600 may be trained based on the backpropagation algorithm. For preventing overfitting, methods of regularization may be used, e.g. dropout of nodes 612-620, stochastic pooling, use of artificial data, weight decay based on the L1 or the L2 norm, or max norm constraints. Different loss functions may be combined for training the same neural network to reflect the joint training objectives. A subset of the neural network parameters may be excluded from optimization to retain the weights pretrained on another datasets.

Any machine training architecture for segmentation may be used. Similarly for other tasks described herein, different machine training architectures may be used. For example, U-Net is used. A convolutional-to-transposed-convolutional network is used. One segment of layers or units applies convolution to increase abstractness or compression. The most abstract feature values are then output to another segment. The other segment of layers or units then applies transposed convolution to decrease abstractness or compression, resulting in outputting of an indication of class membership by location. The architecture may be a fully convolutional network. Other deep networks may be used.

Referring back to FIG. 7, at Act A130, a plurality of images of a LAA 26 of the patient are acquired. Similar to Act A110, the ultrasound scanner uses an ICE catheter 210 to image the heart region of the patient. Images of the LAA 26 may be acquired. In an embodiment, whether or not the LAA 26 is visible in the images is determined. If the acquired images do not include the LAA 26, a notification may be provided. For the procedure, the transducer of the ICE catheter 210 scans a plane. The scan plane is oriented based on a position of the catheter. As the catheter moves (e.g., translates or rotates), different scan planes are scanned. Each scan generates a frame of data representing the scan plane at that time. The frame of ultrasound data may be scalar values or display values (e.g., RGB) in a polar coordinate or Cartesian coordinate format. The frame of ultrasound data may be a B-mode, color flow, or other ultrasound image.

At Act A140, the system determines, based on the model, if the plurality of images of the LAA 26 are sufficient to accurate estimate dimensions of a respective LAA closure device. Sufficiently, for example, may mean that at least 80, 90, 95% of the LAA/LA ostia are visible in at least one image so that an accurate assessment may be performed. Whether or not an image is sufficient for estimating the size of the LAA for an LAAC device may be determined based on a device manufacturer's recommendations for the deployment of a device. Different devices and device manufacturer may require different measurements or values for anatomical features. For instance, a device manufacturer may require that the diameter of the LAAC opening be measured with an accuracy of 2 mm. An image is sufficient if it shows a diameter of the LAA that is within 2 mm of the actual diameter of the LAA. Since there may be some uncertainty in the model recovered from the ICE images, the diameter measured from the model may only be known with a 90% accuracy. So, the system would have as an output that the current image is sufficient with a 90% probability given that the diameter seen on an image is within 2 mm of the maximum diameter as measured on the model.

In an embodiment, one or more of the images of the LAA 26 are registered to the 3D model to determine the orientation of the scan plane in relation to other features of the 3D heart model including, for example, the LA ostia. Features, for example, identified landmarks in the images of the LAA 26 may be registered/matched with related features in the 3D model. The orientation may be derived therefrom. In an embodiment, the features are identified by segmenting the images of the LAA 26, using, for example, a machine trained network as described above that is configured for segmentation. In an embodiment, at act A145, an uncertainty in the ICE frame alignment and uncertainty in the anatomical model is determined and used to identify an uncertainty in specific measurements such as LAA ostia 205 diameter. The uncertainty may be provided to an operator so that they can determine whether or not to acquire a different view. The uncertainty of the sizing measurement may be used in determining whether a device would be appropriate for a LAAC procedure.

At Act A150, when the plurality of images of the LAA 26 are sufficient, an appropriate LAA closure device is specified. In an embodiment, a device may be identified prior to performing the procedure. The plurality of images of the LAA 26 may be used to determine if the device is appropriate by, for example, checking the estimated anatomical feature values against the device specification. In an embodiment, multiple measurements of the LAA 26 are computed and compared against predicted measurements from the LA model. Thes measurements may include not just a measure of the LAA ostia 205 diameter but any measurement of the size or shape of the LAA 26 that is used in choosing a device for an LAA closure. For example, the LAA ostium is measured from the pulmonary vein ridge to the junction of the LA and LAA 26. A landing zone (area within the LAA 26 where the device will be positioned) is measured at 10 mm within the orifice at an angle that is perpendicular to the neck axis. Another important distance to be measured is the maximum length of the anchoring lobe to confirm that this lobe has enough space to accommodate the selected device. Different LAAC devices may be used for different patients based on the measurements. Many manufacturers of LAA closure devices provide solutions that vary in size. If the only selection among devices is based on the size then this is referred to as "sizing" the device. However, additional anatomical measurements other than size may be computed and used to aid in sizing or in choosing between different manufacturers devices.

When the plurality of images of the LAA 26 are not sufficient, an operator is instructed to acquire additional images of the LAA 26. Instructions on how to better position the ICE catheter 210 in order to get an ICE image that will better support measurements of the LAA 26 useful for choosing an LAA closure device may be provided. For example, the instructions may include rotating or adjusting the location of the catheter so that the orientation of the transducer provides an image slice that fully depicts the LA ostia.

In an embodiment, the 2D ICE procedure provides adequate visualization of the LAA 26 and can be used as an alternative to TEE in guiding LAA occlusion procedures. Embodiments provide an estimated model of the anatomy to guide 2D ICE imaging of the LAA ostia 205 to best choose a device for the LAA closure. In addition, the guidance may be used to provide 2D ICE images that rule out LAA thrombus, select the device size by measuring the dimensions of the landing zone, guide the transseptal puncture, verify positioning of the delivery sheath in the LAA 26, aid device delivery and confirm stability before and after release, check for peridevice leaks with color Doppler flow imaging, and monitor for complications such as cardiac tamponade.

It is to be understood that the elements and features recited in the claims may be combined in different ways to produce new claims that likewise fall within the scope of the present invention. Thus, whereas the dependent claims below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The following is a list of non-limiting illustrative embodiments disclosed herein:

Illustrative embodiment 1. A method for left atrial appendage assessment, the method comprising: acquiring a plurality of images of a left atrium of a patient; generating a model of the left atrium from the plurality of images of the left atrium; acquiring a plurality of images of a left atrial appendage of the patient; determining, based on the model, if the plurality of images of the left atrial appendage are sufficient to accurately estimate a specification of an appropriate left atrial appendage closure device; and computing and providing, when the plurality of images of the left atrial appendage are sufficient, an anatomical measurement of the left atrial appendage or providing, when the plurality of images are not sufficient, instructions for an operator to acquire additional images of the left atrial appendage.

Illustrative embodiment 2. The method according to illustrative embodiment 1, further comprising: identifying the appropriate left atrial appendage closure device based on the anatomical measurement of the left atrial appendage.

Illustrative embodiment 3. The method according to illustrative embodiment 2, further comprising: performing a left atrial appendage closure procedure using the appropriate left atrial appendage closure device.

Illustrative embodiment 4. The method according to one of the preceding embodiments, wherein acquiring comprises acquiring two dimensional images using an ICE ultrasound imaging system.

Illustrative embodiment 5. The method according to one of the preceding embodiments, wherein the model comprises a three dimensional segmentation of the left atrium of the patient.

Illustrative embodiment 6. The method according to one of the preceding embodiments, wherein generating the model comprises: determining positions of scan planes within a cardiac system of the patient for the plurality of images of the left atrium; forming an ICE volume from the plurality of images of the left atrium and the positions; and generating a three-dimensional segmented model from input of the ICE volume to a machine learned network.

Illustrative embodiment 7. The method according to illustrative embodiment 6, wherein determining if the plurality of images of the left atrial appendage are sufficient comprises: registering one or more of the plurality of images to the three-dimensional segmented model; and checking that a full diameter of a left atrial appendage ostia is present in at least one image of the plurality of images of the left atrial appendage using a position of the at least one image relative to the model.

Illustrative embodiment 8. The method according to one of the preceding embodiments, wherein determining comprises: providing an uncertainty measurement in the model and in an image frame position to determine an estimate of a probability that a left atrial appendage ostia diameter has been measured to a certain confidence.

Illustrative embodiment 9. The method according to one of the preceding embodiments, wherein providing further comprises: one or more additional measurements of a size or shape of the left atrial appendage that is used in choosing a device for an left atrial appendage closure.

Illustrative embodiment 10. The method according to one of the preceding embodiments, wherein the instructions are based on simulated alternative views from the model of the left atrium that a ICE catheter could reach that would allow for an accurate calculation of a left atrial appendage ostia diameter.

Illustrative embodiment 11. A system for left atrial appendage device selection, the system comprising: a 2D ICE imaging system configured to acquire left atrium image data of a left atrium of a patient and left atrial appendage image data of a left atrial appendage of the patient; and an imaging processor configured to generate a three dimensional model of the left atrium of the patient from the left atrium image data, the imaging processor further configured to register the left atrial appendage image data to the three dimensional model and determine that the left atrial appendage is sufficiently visualized in the left atrial appendage image data; wherein the imaging processor is further configured to compute at least one anatomical measurement of the left atrial appendage and select a device for an left atrial appendage closure procedure based on at the at least one anatomical measurement.

Illustrative embodiment 12. The system according to one of the preceding embodiments, wherein the left atrium is sufficiently visualized when a left atrial appendage ostia diameter has been measured up to a certain confidence.

Illustrative embodiment 13. The system according to one of the preceding embodiments, wherein the imaging processor is further configured to determine that the left atrial appendage is not sufficiently visualized in the left atrial appendage image data, wherein the imaging processor is configured to generate instructions to an operator to acquire additional image data of the left atrial appendage.

Illustrative embodiment 14. The system according to one of the preceding embodiments, wherein the three dimensional model is generated by segmenting and combining a plurality of scan planes from the left atrium image data.

Illustrative embodiment 15. The system of illustrative embodiment 14, wherein generating the three dimensional model comprises: determining positions of scan planes within a cardiac system of the patient for the left atrium image data; forming an ICE volume from the scan planes and the positions; and generating a three-dimensional segmented model from input of the ICE volume to a machine learned network.

Illustrative embodiment 16. The system according to one of the preceding embodiments, further comprising: a display configured to display the left atrium image data, the left atrial appendage image data, and/or the three dimensional model of the left atrium.

Illustrative embodiment 17. A non-transitory computer implemented storage medium that stores machine-readable instructions executable by at least one processor for left atrial appendage assessment, the machine-readable instructions comprising: acquiring a plurality of images of a left atrium of a patient; generating a model of the left atrium from the plurality of images of the left atrium; acquiring a plurality of images of a left atrial appendage of the patient; determining, based on the model, if the plurality of images of the left atrial appendage are sufficient to accurately estimate a specification of a left atrial appendage closure device; and computing and providing, when the plurality of images of the left atrial appendage are sufficient, an anatomical measurement of the left atrial appendage or providing, when the plurality of images are not sufficient, instructions for an operator to acquire additional images of the left atrial appendage.

Illustrative embodiment 18. The non-transitory computer implemented storage medium according to one of the preceding embodiments, wherein the instructions for generating the model comprise: determining positions of scan planes within a cardiac system of the patient for the plurality of images of the left atrium; forming an ICE volume from the plurality of images of the left atrium and the positions; and generating a three-dimensional segmented model from input of the ICE volume to a machine learned network.

Illustrative embodiment 19. The non-transitory computer implemented storage medium according to one of the preceding embodiments, wherein the instructions for determining comprise: registering the plurality of images of the left atrial appendage to the model of the left atrium; and determining if a full view of a diameter of the left atrial appendage is visualized in the plurality of images of the left atrial appendage.

Illustrative embodiment 20. The non-transitory computer implemented storage medium according to one of the preceding embodiments, wherein acquiring is performed using a 2D ICE imaging system.

The invention claimed is:

1. A method for left atrial appendage assessment, the method comprising:

acquiring a plurality of images of a left atrium of a patient;

generating a model of the left atrium from the plurality of images of the left atrium;

acquiring a plurality of images of a left atrial appendage of the patient;

determining, based on the model, if the plurality of images of the left atrial appendage are sufficient to accurately estimate a specification of an appropriate left atrial appendage closure device by estimating a probability that a diameter of a left atrial appendage ostia has been measured to a predefined accuracy based on a geometric uncertainty in the model and a position of an image frame relative to the model; and computing and providing, when the probability meets a threshold, an anatomical measurement of the left atrial appendage or providing, when the probability does not meet the threshold, instructions for an operator to acquire additional images of the left atrial appendage, wherein the instructions identify a target catheter position to acquire a subsequent image and are based on one or more simulated alternative views generated from the model.

2. The method of claim 1, further comprising:

identifying the appropriate left atrial appendage closure device based on the anatomical measurement of the left atrial appendage.

3. The method of claim 2, further comprising:

performing a left atrial appendage closure procedure using the appropriate left atrial appendage closure device.

4. The method of claim 1, wherein acquiring comprises acquiring two dimensional images using an ICE ultrasound imaging system.

5. The method of claim 1, wherein the model comprises a three dimensional segmentation of the left atrium of the patient.

6. The method of claim 1, wherein generating the model comprises:

determining positions of scan planes within a cardiac system of the patient for the plurality of images of the left atrium;

forming an ICE volume from the plurality of images of the left atrium and the positions; and generating a three-dimensional segmented model from input of the ICE volume to a machine learned network.

7. The method of claim 6, wherein determining if the plurality of images of the left atrial appendage are sufficient comprises:

registering one or more of the plurality of images to the three-dimensional segmented model; and checking that a full diameter of a left atrial appendage ostia is present in at least one image of the plurality of images of the left atrial appendage using a position of the at least one image relative to the model.

8. The method of claim 1, wherein providing further comprises:

one or more additional measurements of a size or shape of the left atrial appendage that is used in choosing the appropriate left atrial appendage closure device.

9. A non-transitory computer implemented storage medium that stores machine-readable instructions executable by at least one processor for left atrial appendage assessment, the machine-readable instructions comprising:

acquiring a plurality of images of a left atrium of a patient;

generating a model of the left atrium from the plurality of images of the left atrium;

acquiring a plurality of images of a left atrial appendage of the patient;

determining, based on the model, if the plurality of images of the left atrial appendage are sufficient to accurately estimate a specification of a left atrial appendage closure device by estimating a probability that a diameter of a left atrial appendage ostia has been measured to a predefined accuracy based on a geometric uncertainty in the model and a position of an image frame relative to the model; and computing and providing, when the plurality of images of the left atrial appendage are sufficient, an anatomical measurement of the left atrial appendage or providing, and when the plurality of images are not sufficient, instructions for an operator to acquire additional images of the left atrial appendage, wherein the instructions identify a target catheter position to acquire a subsequent image and are based on one or more simulated alternative views generated from the model.

10. The non-transitory computer implemented storage medium of claim 9, wherein the instructions for generating the model comprise:

determining positions of scan planes within a cardiac system of the patient for the plurality of images of the left atrium;

forming an ICE volume from the plurality of images of the left atrium and the positions; and generating a three-dimensional segmented model from input of the ICE volume to a machine learned network.

11. The non-transitory computer implemented storage medium of claim 9, wherein the instructions for determining comprise:

registering the plurality of images of the left atrial appendage to the model of the left atrium; and determining if a full view of a diameter of the left atrial appendage is visualized in the plurality of images of the left atrial appendage.

12. The non-transitory computer implemented storage medium of claim 9, wherein acquiring is performed using a 2D ICE imaging system.

* * * * *